(12) United States Patent
Repke et al.

(10) Patent No.: US 6,943,169 B2
(45) Date of Patent: Sep. 13, 2005

(54) QUINOLINONE DERIVATIVES AND USES THEREOF

(75) Inventors: David Bruce Repke, Milpitas, CA (US); Russell Stephen Stabler, Boulder Creek, CA (US); Ralph New Harris, III, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 10/797,545

(22) Filed: Mar. 10, 2004

(65) Prior Publication Data

US 2004/0186092 A1 Sep. 23, 2004

Related U.S. Application Data

(60) Provisional application No. 60/453,574, filed on Mar. 11, 2003.

(51) Int. Cl.[7] ................. A61K 31/497; C07D 403/10
(52) U.S. Cl. .................. 514/252.13; 514/212.07; 514/312; 540/523; 544/363; 546/157; 546/158
(58) Field of Search ............... 514/252.13, 212.07, 514/312, 341; 544/363, 360; 540/523; 546/157, 158, 268.1

(56) References Cited

U.S. PATENT DOCUMENTS

| | | | |
|---|---|---|---|
| 3,733,321 A | 5/1973 | Krapcho | |
| 4,078,062 A | 3/1978 | Krapcho | |
| 6,410,536 B1 | 6/2002 | Dudley et al. | |
| 2004/0024210 A1 | 2/2004 | Johanssen et al. | |

FOREIGN PATENT DOCUMENTS

| | | |
|---|---|---|
| WO | WO 99/50254 A1 | 10/1999 |
| WO | WO 99/50257 A1 | 10/1999 |
| WO | WO 99/50263 A1 | 10/1999 |
| WO | WO 01/12187 A2 | 2/2001 |
| WO | WO 01/57003 A1 | 8/2001 |
| WO | WO 01/57019 A1 | 8/2001 |
| WO | WO 01/74775 A1 | 10/2001 |

OTHER PUBLICATIONS

Rogers et al, Psychopharmacology, vol. 158, p. 114–119 (2001).*

Woolley et al, Neuropharmacology, vol. 41, p. 210–219 (2001).*

Riemer et al , J. Med. Chem., vol. 66, p. 1273–1276 (20030.*

Dawson et al, BR. J. of Pharmacology, vol. 130, p. 23–26 (2000).*

Dawson et al, Br. J. of Neuropsychopharmacology, vol. 25(5), p. 663–668 (2001).*

Woolley et al, Psychoparmacology, vol. 170, p. 358–367 (2003).*

Branchek et al, Annual Rev. Pharmacol. Toxicology, vol. 40, p. 319–334 (2001).*

Ca 98:83656, "noradrenaline and 5–hydroxytryptamine modulation of brain dopamine function: implications for the treatment o Parkinson's disease", Jenner et. al., British Journal of Clinical Pharmacology (1983), 15, Supp. 2, 277–89.*

\* cited by examiner

*Primary Examiner*—Bernard Dentz
(74) *Attorney, Agent, or Firm*—Robert C. Hall

(57) ABSTRACT

The invention provides compounds of the formula:

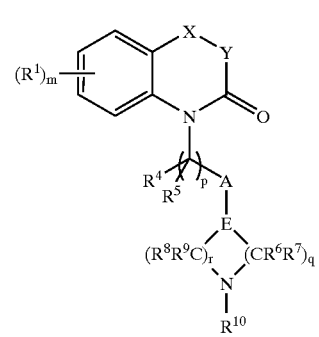

and pharmaceutically acceptable salts or prodrugs thereof, wherein m, p, q, r, A, E, X, Y, $R^1$, $R^4$, $R^5$, $R^6$, $R^7$, $R^8$, $R^9$ and are as defined herein. The invention also provides methods for preparing, compositions comprising, and methods for using compounds of formula I.

32 Claims, No Drawings

QUINOLINONE DERIVATIVES AND USES THEREOF

CROSS-REFERENCE

This application claims the benefit of priority of U.S. Provisional Patent Application Serial No. 60/453,574, filed Mar. 11, 2003, which is incorporated herein by reference in its entirety.

FIELD OF THE INVENTION

This invention relates to substituted benzoxazinone compounds, and associated compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia, obesity and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8.

While some 5-HT6 modulators have been disclosed, there continues to be a need for compounds that are useful for modulating 5-HT6.

SUMMARY

The invention provides compounds of the formula I:

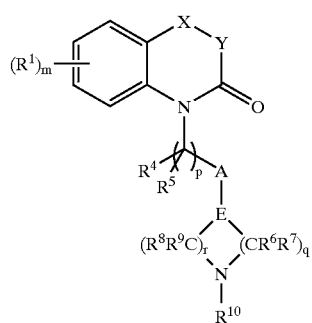

and pharmaceutically acceptable salts or prodrugs thereof, wherein:

m is from 0 to 4;

p is from 1 to 3;

q is from 1 to 3;

r is from 1 to 3;

A is arylene or heteroarylene;

E is N or C;

X is O, S or —$CR^aR^b$— wherein $R^a$ and $R^b$ each independently is hydrogen or alkyl;

each $R^1$ independently is halo, alkyl, haloalkyl, heteroalkyl, hydroxy, nitro, alkoxy, cyano, —$S(O)_sR^c$, —$NR^cR^d$, —$C(=O)$—$NR^cR^d$, —$SO_2$—$NR^cR^d$—N($R^c$—$C(=O)$—$R^d$ or —$C(=)$—$R^c$, wherein s is from 0 to 2 and $R^c$ and $R^d$ each independently is hydrogen or alkyl;

Y is —$(CR^2R^3)_n$— wherein n is 1 or 2 and $R^2$ and $R^3$ each independently is hydrogen or alkyl, or X and Y together form an alkenylene group;

$R^4$, $R^5$, $R^6$, $R^7$, $R^8$, and $R^9$ each independently is hydrogen or alkyl; and $R^{10}$ is hydrogen, alkyl, arylalkyl, aryloxyalkyl, heteroaryl or heterocyclyl.

The invention also provides methods for preparing the aforementioned compounds. The subject methods may comprise, in certain embodiments, reacting a compound of the formula x:

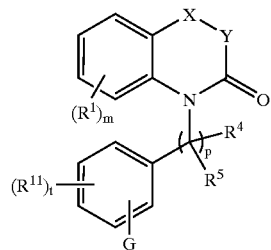

wherein G is a leaving group, t is from 0 to 4, each $R^{11}$ individually is halo, alkyl, haloalkyl, hydroxy, nitro, cyano or alkoxy, and m, p, r. X, Y, $R^1$, $R^4$ and $R^5$ are as defined herein;

with a heterocyclic amine of the formula f:

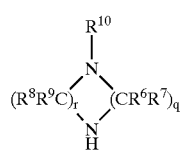

wherein q, r, $R^6$, $R^7$, $R^8$, $R^9$ and $R^{10}$ are as defined herein;

to provide a compound of the formula XIII:

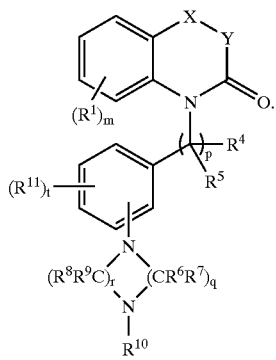

XIII

The invention further provides compositions comprising, and methods for using the aforementioned compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$–$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH═CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, 2-(4-fluorophenyl)-ethyl, 2-(4-methoxyphenyl)-ethyl, and the like are examples of arylalkyl, the aryl portion of which may be optionally substituted.

"Aryloxyalkyl" mean a radical —$R^a$—O—$R^b$ where $R^a$ is an alkylene group and $R^b$ is an aryl group as defined herein, the aryl portion of which may be optionally substituted. Exemplary aryloxyalkyl include 4-fluorophenoxyethyl, 4-methoxyphenoxyethyl, and the like.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Cycloalkoxy" means a moiety of the formula —O—R" where R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", "arylene", phenyl", "phenylene", "heteroaryl", heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkoxy, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R'')_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as
    hydrochloric acid, hydrobromic acid, sulfuric acid, nitric acid, phosphoric acid, and the like;
    or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative quinolinone compounds described herein is shown by the formula:

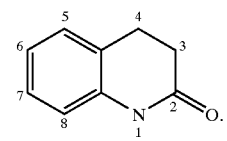

In embodiments of the invention wherein X is a heteroatom, the benzoxazinone numbering system is used herein as shown by the formula:

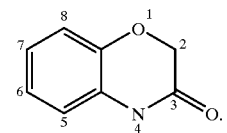

Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

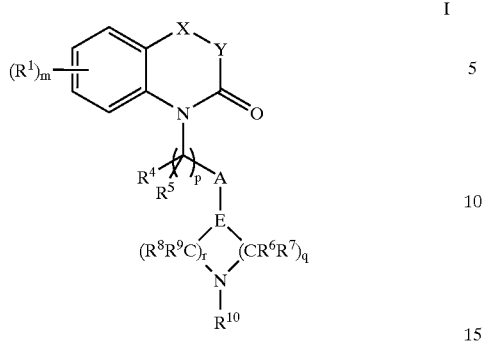

and pharmaceutically acceptable salts or prodrugs thereof, wherein:

m is from 0 to 4;
p is from 1 to 3;
q is from 1 to 3;
r is from 1 to 3;
A is arylene or heteroarylene;
E is N or C;
X is O, S, or —$CR^aR^b$— wherein $R^a$ and $R^b$ each independently is hydrogen or alkyl;
each $R^1$ independently is halo, alkyl, haloalkyl, heteroalkyl, hydroxy, nitro, alkoxy, cyano, —$S(O)_sR^c$, —$NR^cR^d$, —$C(=O)$—$NR^cR^d$, —$SO_2$—$NR^cR^d$—N ($R^c$—$C(=O)$—$R^d$ or —$C(=O)$—$R^c$, wherein s is from 0 to 2 and $R^c$ and $R^d$ each independently is hydrogen or alkyl;
Y is —$(CR^2R^3)_n$— wherein n is 1 or 2 and $R^2$ and $R^3$ each independently is hydrogen or alkyl, or X and Y together form an alkenylene group;
$R^4$, $R^5$, $R^6$, $R^7$, $R^8$, and $R^9$ each independently is hydrogen or alkyl; and
$R^{10}$ is hydrogen, alkyl, arylalkyl, aryloxyalkyl, heteroaryl or heterocyclyl.

In embodiments of the invention where any of $R^1$, $R^2$, $R^3$, $R^4$, $R^5$, $R^6$, $R^7$, $R^8$, $R^9$, $R^{10}$, $R^a$, $R^b$, $R^c$ and $R^d$ are alkyl, they preferably are lower alkyl, i.e. $C_1$–$C_6$alkyl, and more preferably $C_1$–$C_4$alkyl. In many embodiments of the invention wherein A is optionally substituted phenylene, A may be in a "meta" phenylene or 1,3-phenylene configuration with respect to the benzylic carbon adjacent the quinoline 1-position and the piperazinyl moiety. Exemplary substituted phenylenes include halophenylene, haloalkylphenylene, alkylphenylene, alkoxyphenylene and alkylenedioxyphenylene. In embodiments where A is heteroarylene, the heteroarylene may be pyrimidinylene (i.e., a divalent pyrimidinyl radical) or indolylene (divalent indolyl radical).

In embodiments of the invention where $R^{10}$ is arylalkyl, $R^{10}$ is preferably optionally substituted phenylethyl such as 2-(4-fluorophenyl)-ethyl or 2-(4-methoxyphenyl)-ethyl. Where $R^{10}$ is heteroaryl, it is preferably pyrimidyl such as pyrimidin-2-yl. Where $R^{10}$ is heterocyclyl, it is preferably imidazolinyl such as imidazolin-2-yl.

It should be understood that the scope of this invention encompasses not only the various isomers which may exist but also the various mixture of isomers which may be formed. Furthermore, the scope of the present invention also encompasses solvates and salts of compounds of formula I.

In many embodiments of the invention Y is —$(CR^2R^3)_n$—, q is 2 and r is 2, such that compounds of formula I may be represented by the formula II:

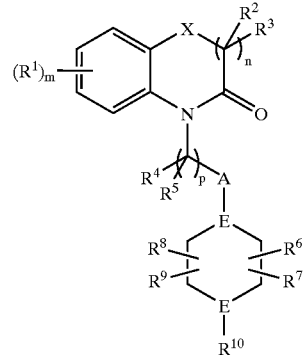

wherein m, n, p, X, A, E, $R^1$, $R^2$, $R^3$, $R^4$, $R^5$, $R^6$, $R^7$, $R^8$, $R^9$ and $R^{10}$ are as defined herein.

In certain embodiments of formula II, p is 1 and A is optionally substituted pheneylene. In such embodiments the compounds of the invention may be represented by the formula III:

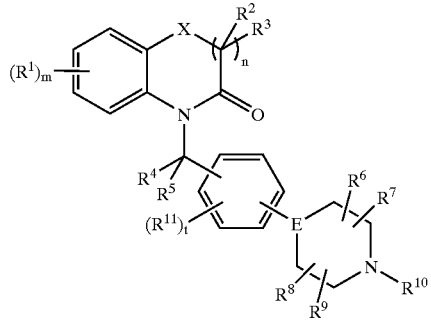

wherein t is from 0 to 4, each $R^{11}$ individually is halo, alkyl, haloalkyl, hydroxy, nitro, cyano or alkoxy, and m, n, X, E, $R^1$, $R^2$, $R^3$, $R^4$, $R^5$, $R^6$, $R^7$, $R^8$, $R^9$ and $R^{10}$ are as defined herein. In certain embodiments t is 0 or 1 and $R^{11}$ is halo, alkyl, haloalkyl, cycloalkoxy or alkoxy, and in specific embodiments $R^{11}$ may be chloro, methyl, trifluoromethyl, methoxy, cyclohexyloxy, or ethoxy. In certain embodiments t is 2 and the pair of $R^{11}$ groups together define an alkylene dioxy radical or moiety such as an ethylene dioxy radical.

In certain embodiments, X is —$CR^aR^b$—, n is 1 and E is N, such that compounds of the invention may more specifically be of the formula IV:

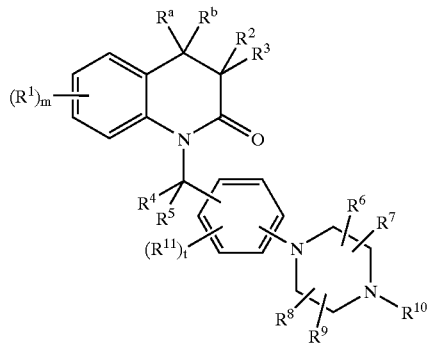

wherein m, t, $R^1$, $R^2$, $R^3$, $R^4$, $R^5$, $R^6$, $R^7$, $R^8$, $R^9$, $R^{10}$, $R^{11}$, $R^a$ and $R^b$ are as defined herein.-

In other embodiments of formula I, X and Y may optionally form an alkenylene group, and in specific embodiments X and Y may form an ethenylene group of the formula: —CH=CH—. The subject compounds in such embodiments may be more specifically represented by the formula V:

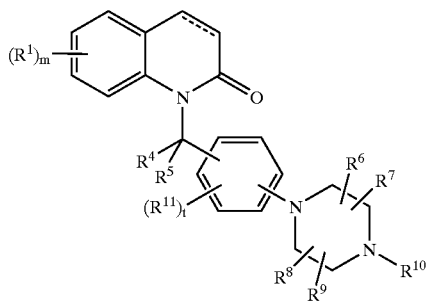

V wherein — represents an optional bond, and m, t, $R^1$, $R^4$, $R^5$, $R^6$, $R^7$, $R^8$, $R^9$ and $R^{10}$ are as defined herein. In specific embodiments of formula V, $R^4$, $R^5$, $R^6$, $R^7$, $R^8$, $R^9$ and $R^{10}$ are hydrogen, and the optionally substituted phenylene moiety is in a "meta" configuration (i.e., a 1,3-phenylene configuration) with respect to the location of the benzylic carbon proximate to the nitrogen at the 1-position of the quinolinone ring system and the piperazinyl group. In such embodiments the compounds of the invention may be represented by the formula VI:

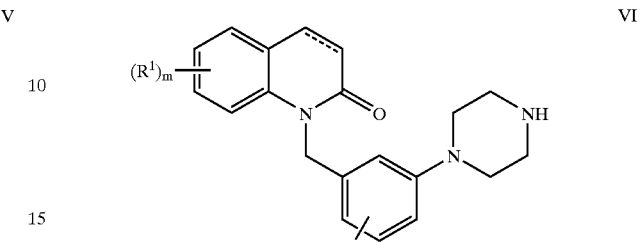

VI wherein — represents an optional bond, and m, t, $R^1$ and $R^{11}$ are as defined herein.

Representative compounds in accordance with the invention are shown in Table 1 together with mass spectrum M+H and experimental examples (described below) associated with each compound.

TABLE 1

| | Name (Autonom ®) | Structure | Example | M + H |
|---|---|---|---|---|
| 1 | 1-(3-Piperazin-1-yl-benzyl)-3,4-dihydro-1H-quinolin-2-one | 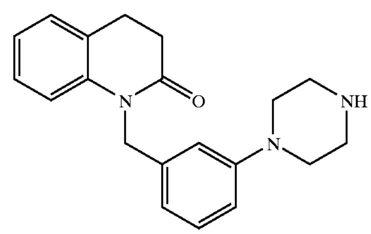 | 1 | 322 |
| 2 | 1-(4-Methoxy-3-piperazin-1-yl-benzyl)-3,4-dihydro-1H-quinolin-2-one | 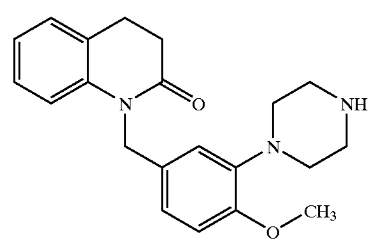 | 1 | 352 |
| 3 | 1-(3-Chloro-5-piperazin-1-yl-benzyl)-3,4-dihydro-1H-quinolin-2-one | 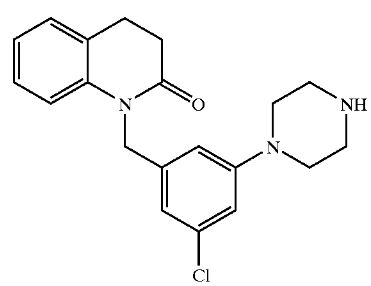 | 1 | 357 |

TABLE 1-continued

| | Name (Autonom ®) | Structure | Example | M + H |
|---|---|---|---|---|
| 4 | 1-(3-Methoxy-5-piperazin-1-yl-benzyl)-3,4-dihydro-1H-quinolin-2-one | 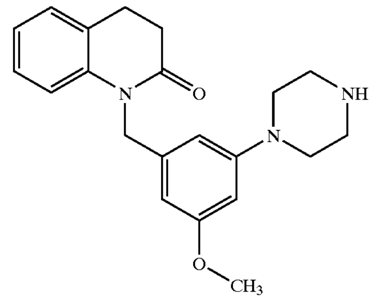 | 1 | 352 |
| 5 | 6-Chloro-1-(3-chloro-5-piperazin-1-yl-benzyl)-3,4-dihydro-1H-quinolin-2-one | 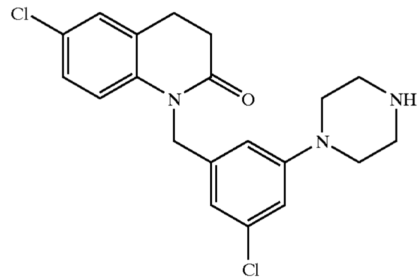 | 1 | 391 |
| 6 | 1-(3-Cyclopentyloxy-5-piperazin-1-yl-benzyl)-3,4-dihydro-1H-quinolin-2-one | 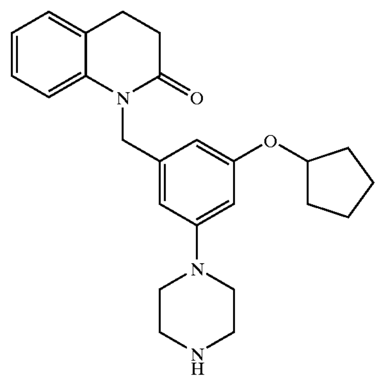 | 1 | 407 |
| 7 | 1-(3-Hydroxy-5-piperazin-1-yl-benzyl)-3,4-dihydro-1H-quinolin-2-one | 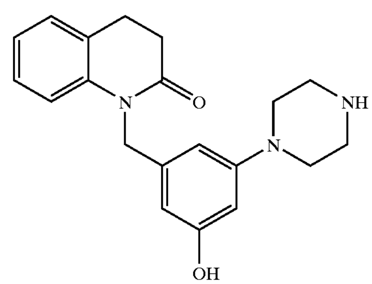 | 1 | 338 |
| 8 | 1-(3-Ethoxy-5-piperazin-1-yl-benzyl)-3,4-dihydro-1H-quinolin-2-one | 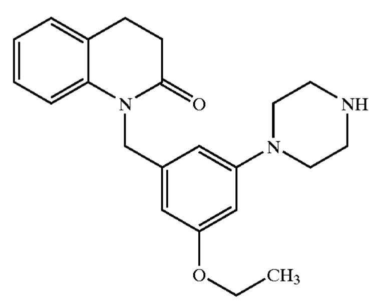 | 1 | 366 |

TABLE 1-continued

| Name (Autonom ®) | Structure | Example | M + H |
|---|---|---|---|
| 9 1-[3-Methoxy-5-(4-methylpiperazin-1-yl)-benzyl]-3,4-dihydro-1H-quinolin-2-one | | 1 | 366 |
| 10 1-(7-Piperazin-1-yl-2,3-dihydro-benz[1,4]dioxin-5-ylmethyl)-3,4-dihydro-1H-quinolin-2-one | | 1 | 380 |
| 11 1-(3-Piperazin-1-yl-5-trifuoromethyl-benzyl)-3,4-dihydro-1H-quinolin-2-one | | 1 | 390 |
| 12 1-(2-Chloro-5-piperazin-1-yl-benzyl)-3,4-dihydro-1H-quinolin-2-one | | 1 | 357 |
| 13 1-(3-Methyl-5-piperazin-1-yl-benzyl)-3,4-dihydro-1H-quinolin-2-one | | 1 | 336 |

TABLE 1-continued

| | Name (Autonom ®) | Structure | Example | M + H |
|---|---|---|---|---|
| 14 | 8-Methoxy-1-(3-Methoxy-5-piperazin-1-yl-benzyl)-3,4-dihydro-1H-quinolin-2-one | 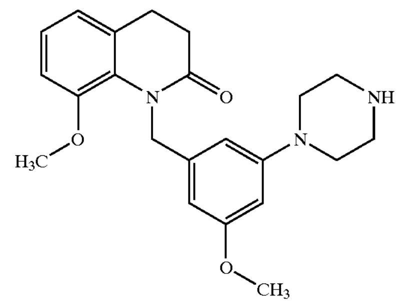 | 1 | 382 |
| 15 | 1-(2-Methoxy-3-piperazin-1-yl-benzyl)-3,4-dihydro-1H-quinolin-2-one | 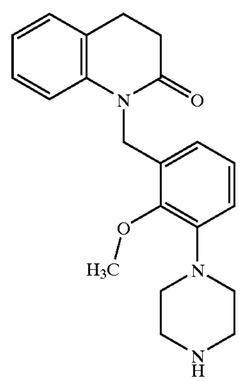 | 1 | 352 |
| 16 | 4-(3-Chloro-5-piperazin-1-yl-benzyl)-7-methoxy-4H-benzo[1,4]oxazin-3-one | 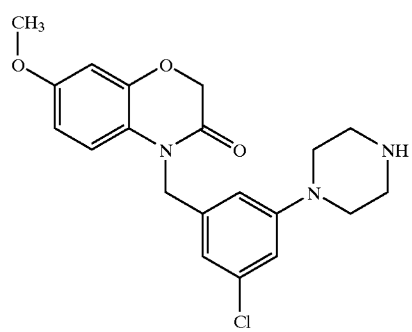 | 2 | 389 |
| 17 | 1-(3-Piperazin-1-yl-benzyl)-1,3,4,5-tetrahydrobenzo[b]azepin-2-one | 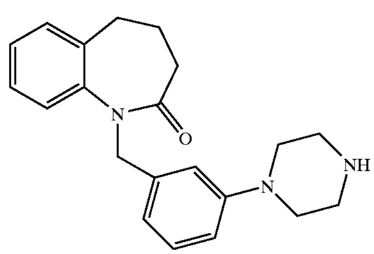 | 3 | 336 |
| 18 | 1-(2-Chloro-6-piperazin-1-yl-pyrimidin-4-ylmethyl)-3,4-dihydro-1H-quinolin-2-one | 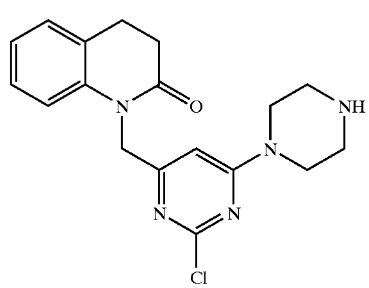 | 1 | 358 |

TABLE 1-continued

| | Name (Autonom ®) | Structure | Example | M + H |
|---|---|---|---|---|
| 19 | 1-(3-Methoxy-5-piperazin-1-yl-benzyl)-1H-quinolin-2-one | 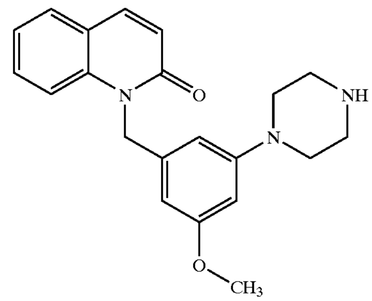 | 1 | 351 |
| 20 | 1-(5-Piperazin-1-yl-1H-indol-3-ylmethyl)-3,4-dihydro-1H-quinolin-2-one | 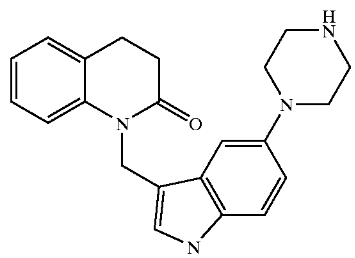 | 1 | 361 |
| 21 | 1-(3-Methoxy-5-{4-[2-(4-methoxy-phenyl)-ethyl]-piperazin-1-yl}benzyl)-1H-quinolin-2-one | 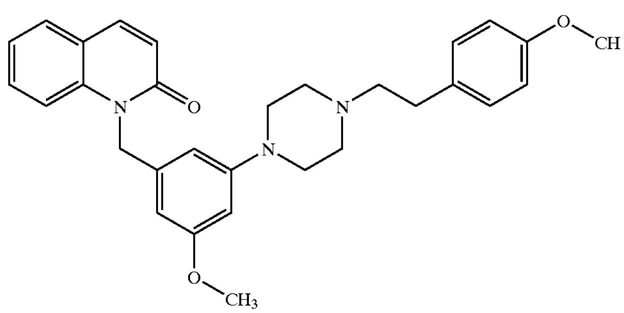 | 1 | 485 |
| 22 | 1-(3-{4-[2-(4-Fluorophenyl)-ethyl]-piperazin-1-yl}-5-methoxybenzyl)-1H-quinolin-2-one | 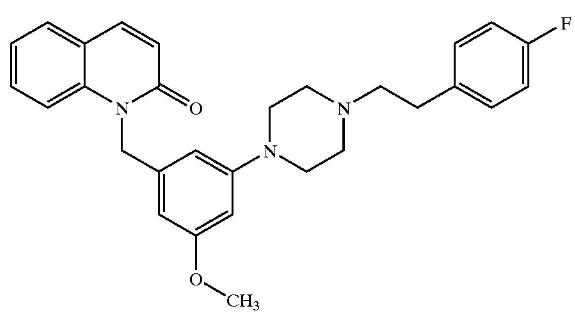 | 1 | 473 |
| 23 | 1-{3-[4-(4,5-Dihydro-1H-imidazol-2-yl)-piperazin-1-yl]-5-methoxybenzyl}-1H-quinolin-2-one | 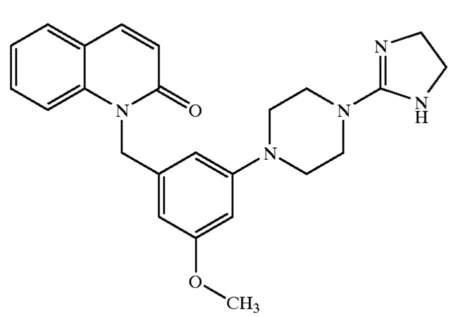 | 1 | 419 |

TABLE 1-continued

| Name (Autonom ®) | Structure | Example | M + H |
|---|---|---|---|
| 24 1-[3-Methoxy-5-(4-pyrimidin-2-yl-piperazin-1-yl)-benzyl]-1Hquinolin-2-one | | 1 | 429 |
| 25 1-(3-{4-[2-(4-Fluoro-phenyl)-ethyl]-piperazin-1-yl}-5-methoxy-benzyl)-8-methoxy-1H-quinolin-2-one | | 1 | 503 |
| 26 1-(3-{4-[2-(4-Fluoro-phenoxy)-ethyl]-piperazin-1-yl}-5-methoxy-benzyl)-1H-quinolin-2-onee | | 1 | 519 |
| 27 8-Methoxy-1-(3-methoxy-5-{4-[2-(4-methoxy-phenyl)-ethyl]-piperazin-1-yl}-benzyl)-1H-quinolin-2-one | | 1 | 515 |

Another aspect of the invention provides a composition comprising a therapeutically effective amount of at least one compound of formula I and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula I.

Another aspect of the present invention provides a method for producing a compound of formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein G is a leaving group and may be the same or different in each occurrence, and m, q, r, t, $R^1$, $R^2$, $R^4$, $R^6$, $R^7$, $R^8$, $R^9$, $R^{10}$ and $R^{11}$ are as defined herein. Specific examples of the procedure of Scheme A are provided in the following Experimental section.

SCHEME A

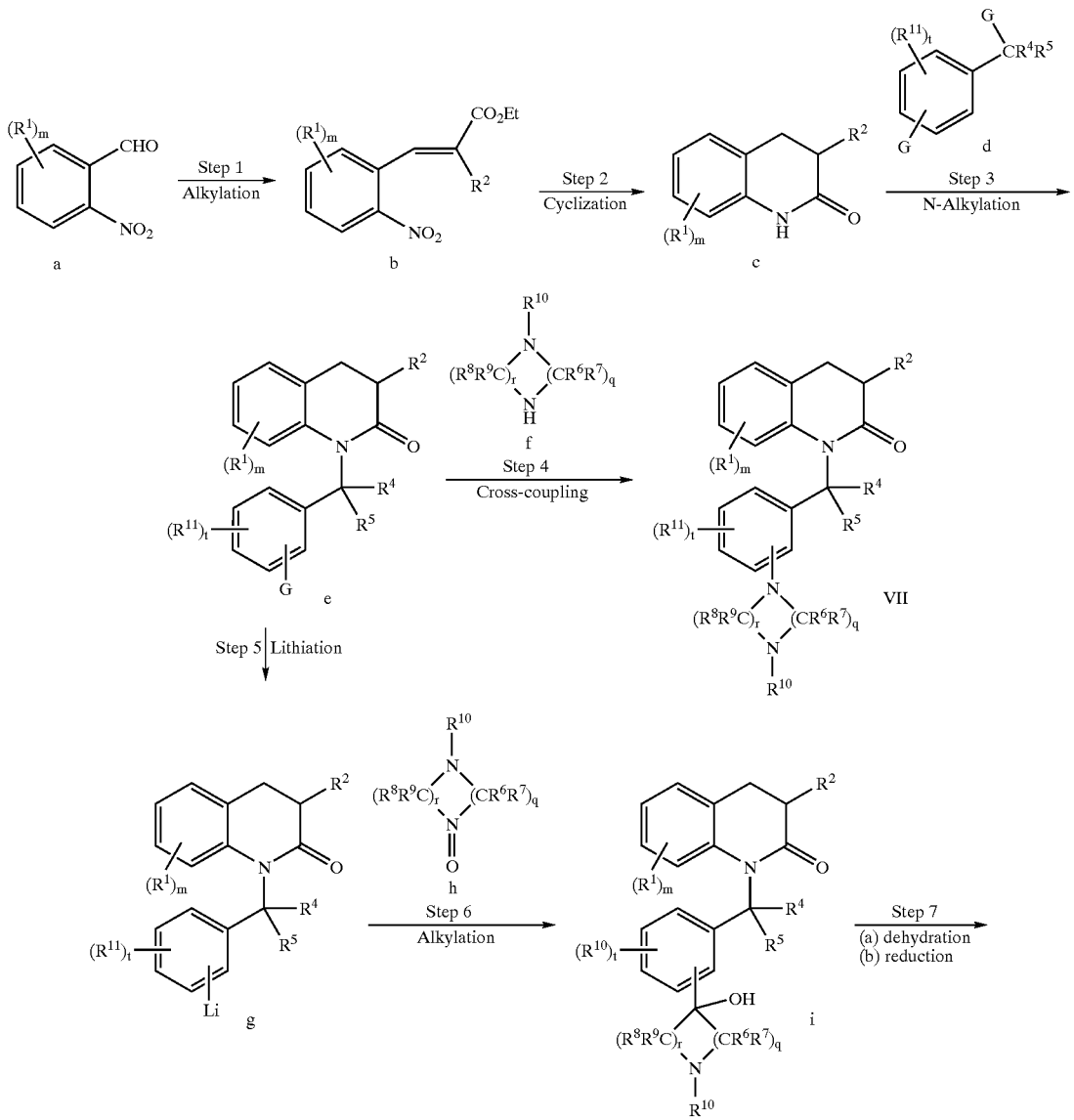

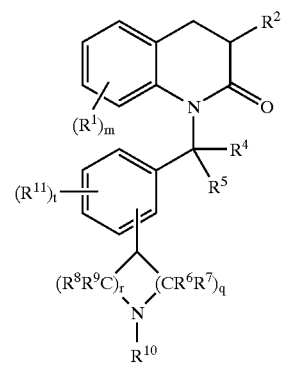

VIII

Numerous synthetic routes to partially hydrogenated quinolinones are known and may be used in preparation of the subject compounds. The synthesis in Steps 1 and 2 of Scheme A represents the procedure reported by Pavia et al., *J. Org. Chem.* (1990) vol. 55(2), pp. 560–564. Briefly, in Step 1 an orthonitrobenzaldehyde a is alkylated via an aldol reaction with a carbethoxyalkylene triphenylphosphorane (not shown) or like agent to provide an aldol condensation product b. Various nitro-substituted benzaldehydes usable in this step are commercially available or can be prepared via well known techniques. For example, nitrobenzoic acids may be reduced to the corresponding benzyl alcohol using borane or like reducing agent, and the benzyl alcohol then selectively oxidized to the corresponding benzaldehyde via pyridinium chlorochromate reduction as reported by Pavia et al., supra.

In Step 2, a cyclization of aldol condensation product b under reducing conditions yields quinolinone c. This cyclization may be achieved, for example, by hydrogenation in the presence of platinum catalyst.

In Step 3, an N-alkylation is carried out by treatment of quinolinone c with strong base, such as a metal hydride under polar aprotic conditions, followed by exposure to alkylating agent d to provide an N-alkylated quinolinone e. The leaving groups G of alkylating agent d, which may be the same or different, are preferably bromo or other halo.

A cross-coupling amination reaction may then be utilized in Step 4 in which the N-alkylated quinolinone e of Step 3 is treated with a heterocyclic amine f in the presence of a palladium catalyst to displace leaving group G and yield a heterocyclyl-substituted quinolinone VII. This cross-coupling reaction may be achieved via heating under non-polar solvent conditions. Where $R^{10}$ is hydrogen, BOC protection or other removable protection strategies may be used to protect the exposed nitrogen of heterocyclic amine f.

The substituted quinolinone VII produced in Step 4 represents a specific embodiment of compounds of formula I, discussed above, wherein X is —CH$_2$—, Y is —CHR$^2$—, n is 1, p is 1, A is optionally substituted phenylene, and E is N.

Numerous variations on the procedure of Steps 1–4 are possible and may be used to provide various compounds of formula 1. One such variation useful for preparation of quinolinones wherein $R^1$ is sensitive to or incompatible with the reducing conditions of step 2, involves reaction of the orthonitrobenzaldehyde a with "Meldrum's ester" in the presence of triethylamine and formic acid to produce an aldol condensation product (not shown). The aldol condensation product can then be esterified and subject to cyclization by heating in the presence of sodium dithionate to provide quinolinone c. This particular procedure is described in *Synthetic Communications*, Vol. 25 p. 3067 (1995).

In another variation, alkylating agent d used in the alkylation of Step 3 may comprise a α-haloalkyl naphthyl compound, α-haloalkylbiphenyl compound, α-haloalkylethylenedioxyphenyl compound, or other α-haloalkylaryl compound. In other embodiments Step 3 may be carried out using α-haloalkyl heteroaryl compounds such as α-haloalkylpyridines, α-haloalkylthiophenes, α-haloalkylindoles, α-haloalkylethylenedioxyphenyl compounds, and the like. In the case of α-haloalkyl heteroaryl compounds, suitable protection group strategies may be employed to avoid unwanted heteroatom alkylation during this step.

In certain embodiments, heterocyclic amine f may be a piperazine of the formula:

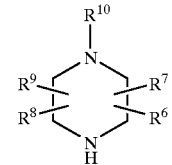

(i.e., q and r each are equal to 2), such that the compound of formula VII is of formula IV discussed above, with $R^3$ shown as hydrogen. Many substituted piperazines of this sort, including N-methyl piperazine and 3,5-dimethylpiperazine for example, are commercially available or prepared by well known techniques and may be used in the procedure of Scheme A.

In other embodiments of the invention, Step 4 may be omitted and Steps 5–7 carried out in place thereof. In Step 5, the N-alkylated quinolinone e prepared in Step 3 is lithiated via treatment with an alkyllithium reagent to provide a lithiated quinolinone g.

An alkylation may then be carried out in Step 6 by reaction of lithiated quinolinone f with a heterocyclyl ketone h to effect formation of compound i. Heterocyclyl ketone h may comprise, for example, an optionally substituted piperidinone or an optionally substituted pyrrolidinone, both of which are commercially available or can be prepared by well-known techniques. Where $R^{10}$ is hydrogen, a BOC, allyl or other protection group may be used to protect the nitrogen heteroatom of ketone h.

Compound i may in turn be dehydrated in Step 7 and then optionally subject to reduction to provide quinolinone derivative VIII. In certain embodiments, dehydration ofcompound i may occur spontaneously. Quinolinone derivative VIII represents a specific embodiment of compounds of formula I wherein, wherein X is —CH$_2$—, Y is —(CR$^2$R$^3$)$_n$— with n being 1 and R$^3$ being hydrogen, p is 1, A is optionally substituted phenylene, and E is CH.

Scheme B below illustrates another synthetic procedure that may be used in preparation of compounds of the invention, wherein G is a leaving group and may be the same or different in each occurrence, and m, n, q, r, t, R$^1$, R$^2$, R$^4$, R$^6$, R$^7$, R$^8$, R$^9$, R$^{10}$ and R$^{11}$ are as defined herein.

SCHEME B

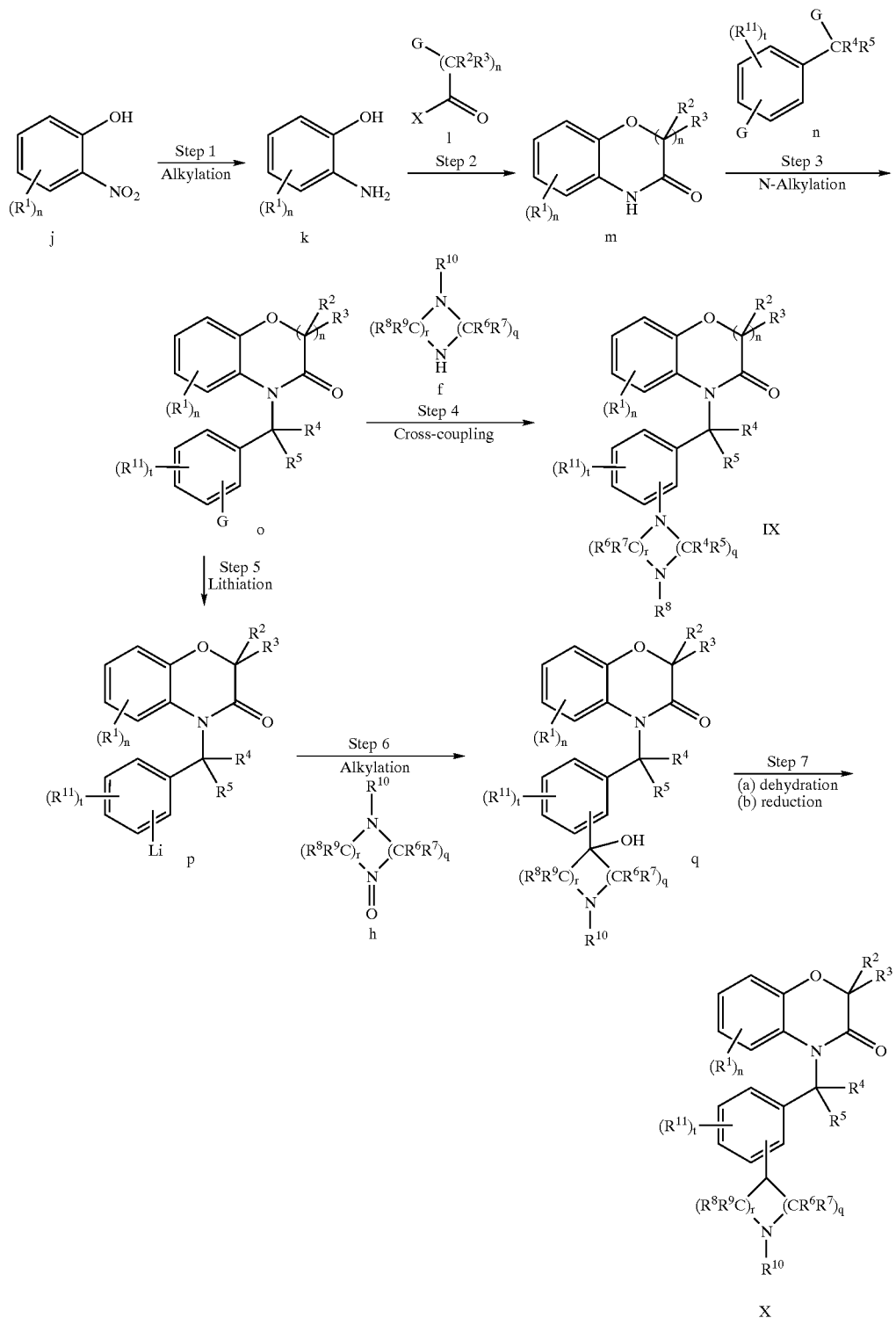

Many synthetic routes to benzoxazinones are known and may be used in the preparation of the subject compounds for embodiments of formula I wherein X is O, and the synthesis outlined in Steps 1 and 2 is only exemplary.

In Step 1 of Scheme B, an ortho nitrophenol i is reduced to an aniline or aminophenol k. This reduction may be carried out under relatively mild, aqueous conditions, using sodium dithionite or like mild reducing agent.

A cyclization is then carried out in Step 2 to provide a benzoxazinone compound m from the aminophenol i generated in Step 1. Where n is 1, for example, the benzoxazinone m is a 2H-1,4-benzoxazin-3(4H)-one, and where n is 2 the compound m is a 2,3-Dihydro-1,5-benzoxazepin-4(5H)-one. The cyclization may be achieved by reaction of the aminophenol i with a 2-halo acid halide l (G is halo) such as chloroacetyl chloride (to provide n=1 and $R^3$, $R^4$ as hydrogen), 2-chloropropionyl chloride (which provides n=1, $R^3$ as methyl and $R^4$ as hydrogen), 3-chloropropionyl chloride (providing n=2 and $R^3$, $R^4$ as hydrogen), 2-chloroisobutyryl chloride (providing n=1, $R^3$ as isopropyl and $R^4$ as hydrogen), 2-chloro-2-methylpropionyl chloride (providing n=1 and $R^3$ and $R^4$ as methyl), and so on. Formation of benzoxazinones in this manner can be achieved under relatively mild polar conditions in the presence of a mild base, as described by Combs et al.; *J. Med. Chem.*; 33; 380–386 1990. The cyclization may also be achieved by reacting k with a 2-hydroxyester under Mitsunobu reaction conditions, as described by Van Hess et al in WO 01/14330. See also *Heterocycles* 1983, vol. 20(8), pp. 1481–1485, for synthesis of substituted benzoxazinones.

In Step 3, an N-alkylation of the benzoxazinone compound m is carried out by treatment of compound m with a strong base under dry, polar aprotic conditions and reaction with an α-haloalkyl aryl compound n to provide the N-arylalkyl-benzoxazinone compound o. The haloalkyl aryl compound n may comprise, for example, benzyl halide, 3-halo-3-phenylpropane, α-methylbenzyl halide, or α-haloalkylphenyl halides according to the desired $R^4$ and $R^5$ substituent configuration.

The alkylation of Step 3 may also be carried out using α-haloalkyl napthyl compounds, α-haloalkylbiphenyl compounds or other α-haloalkylaryl compounds. In other embodiments Step 3 may be carried out using α-haloalkyl heteroaryl compounds such as α-haloalkylpyridines, α-haloalkylthiophenes, α-haloalkylmethylenedioxyphenyl compounds, α-haloalkylethylenedioxyphenyl compounds, and the like. In the case of α-haloalkyl heteroaryl compounds, suitable protection group strategies may be employed to avoid unwanted heteroatom alkylation during this step.

A cross coupling amination reaction is then carried out in Step 4 wherein the N-arylalkyl-benzoxazinone compound o is reacted with a nitrogen-containing heterocycle f in the presence of a palladium catalyst to replace the leaving group G with a heterocyclyl group and provide the heterocyclyl-N-arylalkyl-benzoxazinone compound IX. In many embodiments q and r are 2, such that the heterocycle compound f is a piperazine compound as described above in Example A. Where $R^{10}$ is hydrogen, BOC protection or other removable protection strategies may be used to protect the exposed nitrogen of heterocyclic amine f.

The heterocyclyl-N-arylalkyl-benzoxazinone compound IX is a compound of formula I wherein X is O, Y is —$(CR^2R^3)_n$—, p is 1, q and r are 2, A is optionally substituted phenylene, and E is N. As in the case of Scheme A, many variations on the above procedure are possible and may be used to prepare other compounds of formula I in accordance with the invention.

In other embodiments of the invention, Step 4 of Scheme B may be omitted and Steps 5–7 carried out in place thereof in the manner described above for Scheme A. Thus, in Step 5, the N-alkylated benzoxazinone o of Step 3 is lithiated via treatment with alkyllithium reagent as described above for Scheme A, to provide a lithiated benzoxazinone p. An alkylation may then be carried out in Step 6 by reaction of lithiated benzoxazinone p with heterocyclyl ketone h to yield compound q. Heterocyclyl ketone h may be an optionally substituted piperidinone or an optionally substituted pyrrolidinone as noted above, and a suitable protection strategy for the nitrogen heteroatom may be employed where $R^{10}$ is hydrogen. Compound q may in turn be dehydrated in Step 7 and then optionally subject to reduction to provide benzoxazinone (i.e., quinolinone derivative) X.

The compound X is a compound of formula I wherein X is O, Y is —$(CR^2R^3)_n$—, p is 1, q and r are 2, A is optionally substituted phenylene, and E is C. It is again noted that variations on the above procedure may be used to make other compounds of formula I. Such variations will suggest themselves to those skilled in the art and are considered to be within the scope of this disclosure.

In still other embodiments of the invention, specific compounds of formula I may be prepared according to the procedure shown in Scheme C, wherein G is a leaving group and may the same or different in each occurrence, and m, q, r, t, $R^1$, $R^2$, $R^4$, $R^6$, $R^7$, $R^8$, $R^9$, $R^{10}$ and $R^{11}$ are as defined herein.

SCHEME C

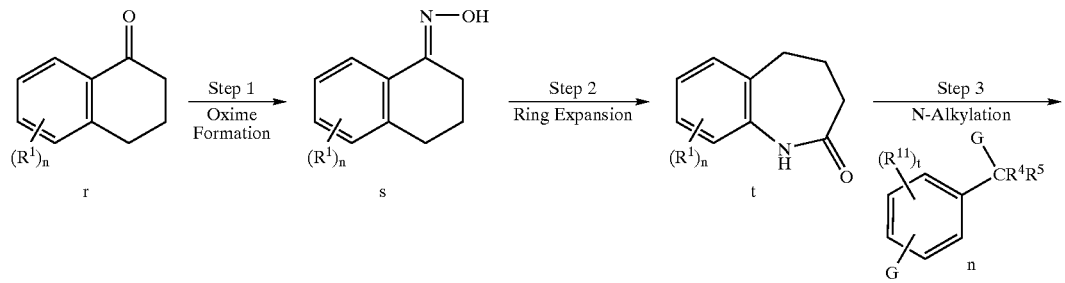

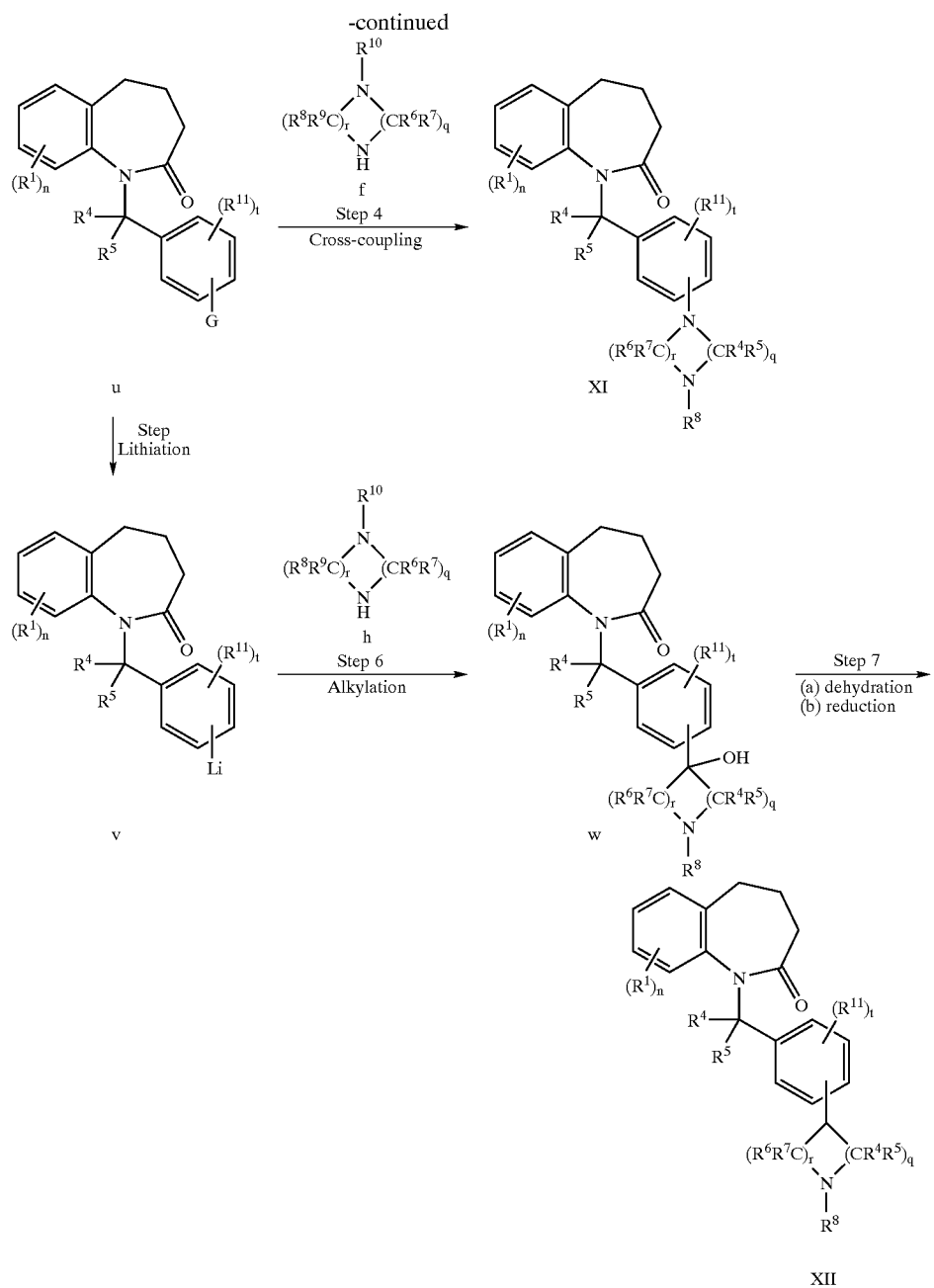

In Step 1 of Scheme C, tetralone r is converted to a tetralone oxime s. This may be achieved by treatment of tetralone r with hydroxylamine under aqueous conditions with heating.

The oxime s of Step 1 undergoes a ring expansion rearrangement in Step 2 to provide a tetrahydrobenzoazepinone t. The rearrangement of Step 2 may be carried out by heating oxime s in the presence of polyphosphoric acid.

In Step 3, the tetrahydrobenzoazepinone t of Step 2 is N-alkylated via treatment with alkylating agent n to yield an N-alkylated tetrahydrobenzoazepinone u. The alkylation of this step may be effected by treatment of tetrahydrobenzoazepinone t with metal hydride, together with alkylating agent n, under polar aprotic conditions. Various alkylating agents may be used in this step as described above according to particular compounds of formula I that are desired.

A cross-coupling amination reaction is used in Step 4 wherein N-alkylated tetrahydrobenzoazepinone u is treated with heterocyclic amine f in the presence of base, trialkylphosphine and a palladium catalyst as described above for Schemes A and B, to provide tetrahydrobenzoazepinone XI. Various heterocyclic amines may be used in this step as related above, to provide various compounds of formula I in accordance with the invention.

Tetrahydrobenzoazepinone XI is a compound of formula I in accordance with the invention wherein X is —$CH_2$—, Y is —$(CH_2)_2$—, p is 1, A is optionally substituted phenyl, and E is N.

Other compounds of the invention may be prepared by omission of Step 4, with Steps 5–7 carried out instead. In a manner similar to that described above for Scheme A and Scheme B, in Step 5 the N-alkylated tetrahydrobenzoazepinone u is lithiated via treatment with alkyllithium reagent to provide a lithiated tetrahydrobenzoazepinone v. An alkylation may then be carried out in Step 6 by reaction of lithiated tetrahydrobenzoazepinone v with heterocyclyl ketone h to yield compound w, which in turn can be dehydrated in Step 7 and then optionally subject to reduction to provide tetrahydrobenzoazepinone XII.

The compound XII is a compound of formula I wherein X is —$CH_2$—, Y is —$(CH_2)_2$—, n is 2, $R^2$ and $R^3$ are hydrogen, p is 1, A is optionally substituted phenyl, and E is C. It should again be noted that variations on the above procedure may be used to make other compounds of formula I, as will be readily apparent to those skilled in the art.

More specific details for producing compounds of formula I are described in the Examples section below.

Utility

The compounds of the invention have selective 5-HT6 receptor affinity and as such are expected to be useful in the treatment of certain central nervous system (CNS) disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder.

Testing

The pharmacology of the compounds of this invention was determined by art recognized procedures. The in vitro techniques for determining the affinities of test compounds at the 5-HT6 receptor in radioligand binding and functional assays are described in Example 4.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvi-nylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof.

Preparation 1

3-Bromo-5-methoxy-benzyl bromide

The synthetic procedures described in this Preparation were carried out according to the process shown in Scheme D.

SCHEME D

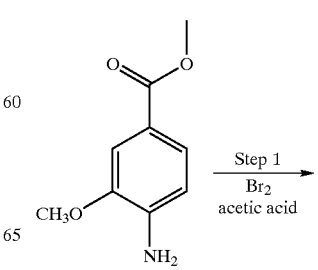

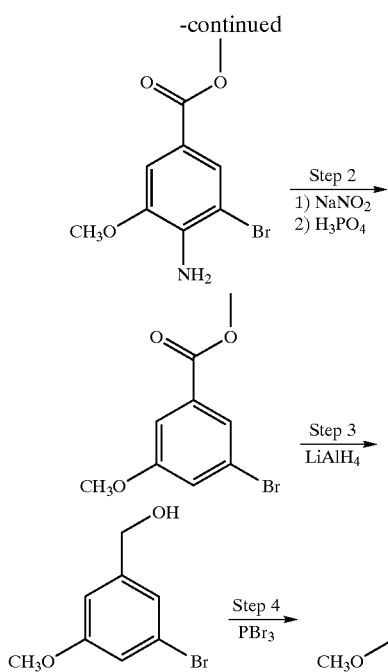

Step 1
Methyl 3-bromo-5-methoxy-4-aminobenzoate

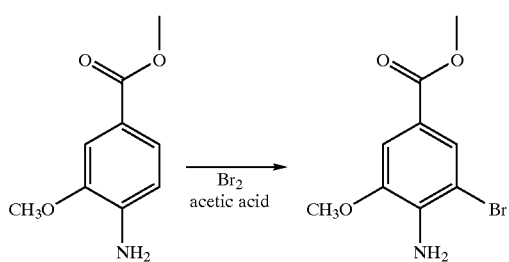

10.5 Grams (55 mmole) of methyl 3-methoxy-4-aminobenzoate was dissolved in 80 ml methanol, and 3.0 ml bromine (55 mmole) in 20 ml acetic acid was added dropwise at room temperature. The solution was stirred for three hours at room temperature and the solvents were evaporated under reduced pressure. The residue was treated with sodium bicarbonate solution and the product was filtered and air-dried to yield 16.5 grams of methyl 3-bromo-5-methoxy-4-aminobenzoate.

Step 2
Methyl 3-bromo-5-methoxybenzoate

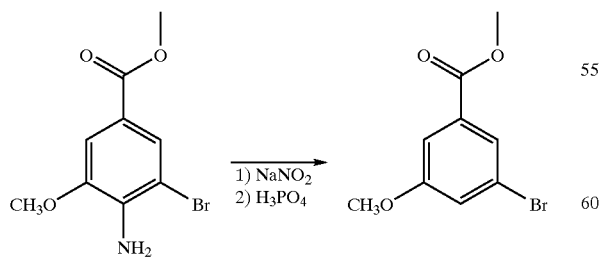

A 500 ml round bottom flask fitted with overhead stirring was charged with 16.5 grams (55 mmole) of methyl 3-bromo-5-methoxy-4-aminobenzoate in 80 ml ethanol, 15 ml sulfuric acid and 20 ml acetic acid. The solution was chilled in an ice bath and 6.6 gms (95 mmole) of sodium nitrite in 30 ml water was added dropwise while maintaining the temperature below 10° C. After stirring an additional 25 minutes, 100 ml of 50% hypophosphoric acid was added and the mixture was stirred cold for 2 hours. The reaction mixture was diluted with 500 ml water, extracted with ether, and then evaporated under reduced pressure to give 13.5 grams of methyl 3-bromo-5-methoxybenzoate as a reddish oil.

Step 3
3-Bromo-5-methoxy benzyl alcohol

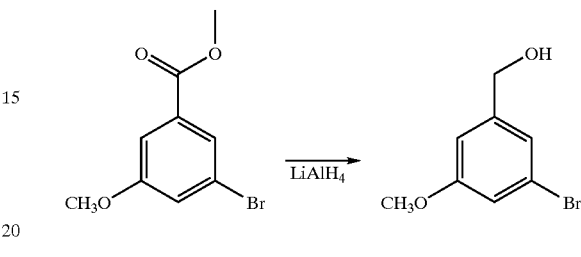

13.5 Grams (55 mmole)) Methyl 3-bromo-5-methoxybenzoate was dissolved in ether and cooled in an ice bath. 33 ml of 1M lithium aluminum hydride was added dropwise. The reaction mix was then quenched cautiously by addition of sodium sulfate decahydrate, then water, and solid residue was removed by filtration. The ether was separated and evaporated under reduced pressure to give 11 gms of 3-bromo-5-methoxy benzyl alcohol as a white solid.

Step 4
3-Bromo-5-methoxy-benzyl bromide

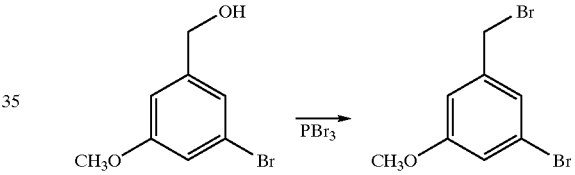

11 Grams (51 mmole) of 3-bromo-5methoxy benzyl alcohol was dissolved in 100 ml methylene chloride and cooled in an ice-bath. 2.0 ml (20 mmole) of phosphorus tribromide was added dropwise to this solution at room temperature, and the mixture was allowed to stir for 10 minutes. Saturated sodium bicarbonate solution was then added, and the mixture was extracted with ether and washed with sodium bicarbonate solution. Evaporation of the ether yielded 12 grams of 3-Bromo-5-methoxy-benzyl bromide as a white solid.

Using the procedure of Example 1 with the appropriate substituted methyl benzoates, the following representative benzyl bromide compounds were also prepared:
  3-bromo-5-hydroxy-benzyl bromide;
  3-bromo-5-ethoxy-benzyl bromide;
  3-bromo-5-trifluoromethyl-benzyl bromide;
  3-bromo-5-methyl-benzyl bromide;
  3-bromo-4-methoxy-benzyl bromide;
  3-bromo-5-cyclopentyloxy-benzyl bromide;
  3-bromo-2-chloro-benzyl bromide; and
  7-bromo-5-bromomethyl-12,3-dihydro-benzo[1,4]dioxine.

Example 1

1-(3-Methoxy-5-piperazin-1-yl-benzyl)-3,4-dihydro-1H-quinoline-2-one

The synthetic procedures described in this Example were carried out according to the process shown in Scheme E.

SCHEME E

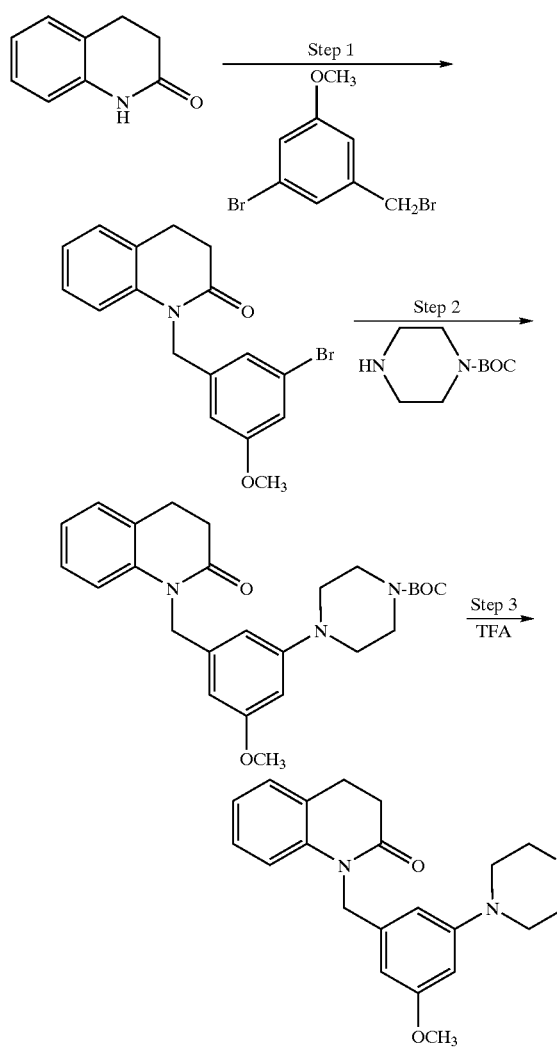

Step 1
4-(3-Bromo-5-methoxy-benzyl)-3,4-dihydro-1H-quinoline-2-one

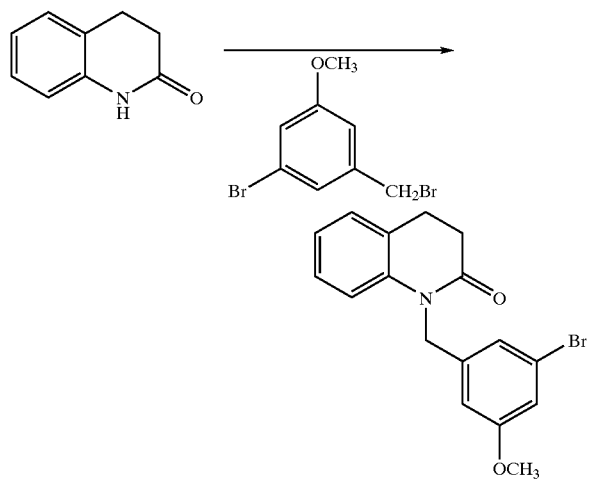

3,4-Dihydro-2(1H)-quinolinone was purchased from Aldrich Chemical Co. (Cat. No. 41,593-6) and used without purification in this step. 0.45 grams of 3,4-dihydro-2(1H)-quinolinone (3.0 mmole) was dissolved in 15 ml dimethylformamide and cooled in an ice bath. 0.2 grams (4.5 mmole) of sodium hydride (60% wt. in oil) was added to this solution, and after 5 minutes 0.84 grams 3-bromo-5-methoxy-benzylbromide (3 mmol) was added thereto all at once. The mixture was stirred at ice bath temperature for 1 hour and then quenched by addition of 1% hydrochloric acid. The reaction mix was extracted with ethyl acetate, which was evaporated under reduced pressure to give an oil, which was chromatographed with medium pressure eluting using 10% ethyl acetate in hexanes to yield 0.8 grams of solid 4-(3-bromo-5-methoxy-benzyl)-3,4-dihydro-1H-quinoline-2-one.

Step 2

1-(3-Methoxy-5-(4-Boc-piperazin-1-yl)-benzyl)-3,4-dihydro-1H-quinoline-2-one

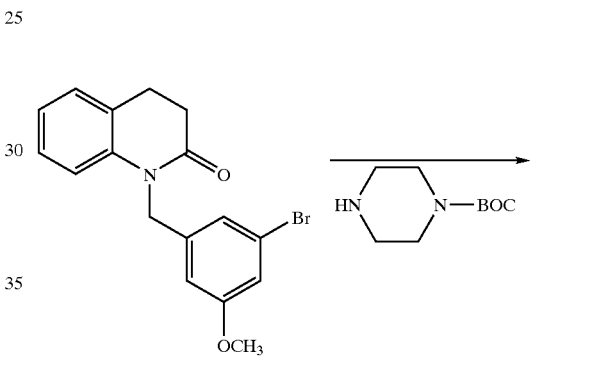

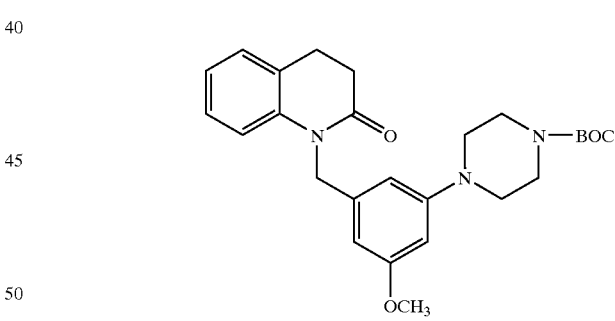

0.8 grams (2.2 mmole) of 4-(3-bromo-5-methoxy-benzyl)-3,4-dihydro-1H-quinoline-2-one, together with 0.44 grams of 1-Boc-Piperazine, 0.025 grams (0.11 mmole) of palladium (II) acetate, 0.023 grams (0.011 mmole) of tri-t-butyl phosphine and 0.23 grams of sodium-t-butoxide) were added to 20 ml of xylenes. The solution was heated to 110° C. under argon for 4 hours. The resulting dark mixture was filtered through celite, the solvent evaporated, and the residue chromatograghed via medium pressure eluting with 20% ethyl acetate in hexanes to yield 0.4 grams of solid 1-(3-methoxy-5-piperazin-1-yl-benzyl)-3,4-dihydro-1H-quinoline-2-one as a white solid.

Step 3
1-(3-Methoxy-5-piperazin-1-yl-benzyl)-3,4-dihydro-1H-quinoline-2-one

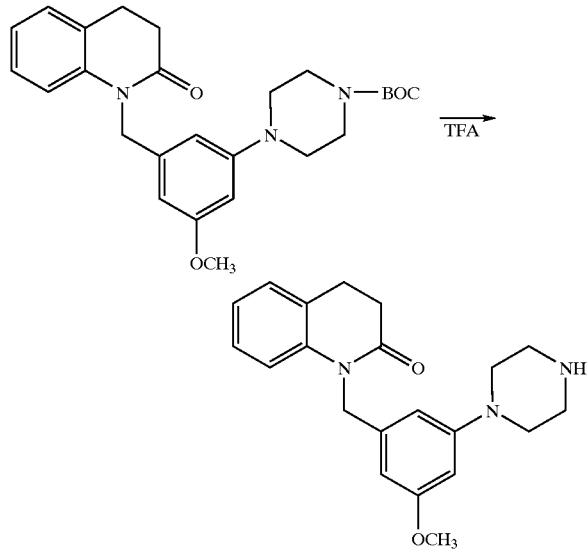

The Boc-protecting group was removed from 1-(3-methoxy-5-piperazin-1-yl-benzyl)-3,4-dihydro-1H-quinoline-2-one by warming the 0.4 grams of product from Step 2 with 5 ml triflouroacetic acid. Excess trifluoroacetic acid was evaporated under reduced pressure and the trifluoroacetate salt was crystallized from ethyl acetate/diethyl ether to yield 0.35 grams of 1-(3-methoxy-5-piperazin-1-yl-benzyl)-3,4-dihydro-1H-quinoline-2-one, M+H=352.

Using the above procedure, but replacing 3-bromo-5-methoxy-benzylbromide in step 1 with the appropriate benzyl bromides prepared as described in Preparation 1, the following compounds were also prepared:

1-(3-Piperazin-1-yl-benzyl)-3,4-dihydro-1H-quinolin-2-one;
  1-(4-Methoxy-3-piperazin-1-yl-benzyl)-3,4-dihydro-1H-quinolin-2-one;
  1-(3-Chloro-5-piperazin-1-yl-benzyl)-3,4-dihydro-1H-quinolin-2-one;
  1-(3-Cyclopentyloxy-5-piperazin-1-yl-benzyl)-3,4-dihydro-1H-quinolin-2-one;
  1-(3-Hydroxy-5-piperazin-1-yl-benzyl)-3,4-dihydro-1H-quinolin-2-one;
  1-(3-Ethoxy-5-piperazin-1-yl-benzyl)-3,4-dihydro-1H-quinolin-2-one;
  1-(7-Piperazin-1-yl-2,3-dihydro-benzo[1,4]dioxin-5-ylmethyl)-3,4-dihydro-1H-quinolin-2-one;
  1-(3-Piperazin-1-yl-5-trifuoromethyl-benzyl)-3,4-dihydro-1H-quinolin-2-one;
  1-(2-Chloro-5-piperazin-1-yl-benzyl)-3,4-dihydro-1H-quinolin-2-one;
  1-(3-Methyl-5-piperazin-1-yl-benzyl)-3,4-dihydro-1H-quinolin-2-one;
  1-(2-Methoxy-3-piperazin-1-yl-benzyl)-3,4-dihydro-1H-quinolin-2-one;
  1-(3-Methoxy-5-piperazin-1-yl-benzyl)-1H-quinolin-2-one; and
  1-(2-Methoxy-3-piperazin-1-yl-benzyl)-3,4-dihydro-1H-quinolin-2-one.

Using the above procedure, but replacing piperazine in step 2 with 1-methylpiperazine, 1-[3-methoxy-5-(4-methylpiperazin-1-yl)-benzyl]-3,4-dihydro-1H-quinolin-2-one was prepared.

Using the above procedure, but replacing 3,4-dihydro-2(1H)-quinolinone in step 1 with 5-chloro-3,4-dihydroquinolin-1-one prepared according to the procedure reported in Bioorganic & Medicinal Chemistry Letters (2000), Vol. 10(14), pp. 1559–1562, and using 3-bromo-2-chloro-benzyl bromide in step 1, the compound 6-Chloro-1-(3-chloro-5-piperazin-1-yl-benzyl)-3,4-dihydro-1H-quinolin-2-one was prepared.

Using the procedure of Example 1, but replacing 3,4-dihydro-2(1H)-quinolinone in step 1 with 8-methoxy-3.4-dihydroquinolin-1-one prepared according to the procedure reported in Journal of Organic Chemistry (1990), Vol. 55(2), pp. 560–564, the compound 8-methoxy-1-(3-Methoxy-5-piperazin-1-yl-benzyl)-3,4-dihydro-1H-quinolin-2-one was prepared.

Also using the procedure of Example 1, but replacing 3-bromo-5-methoxy-benzylbromide respectively with 5-bromo-3-bromomethyl-1H-indole and 4-Bromo-6-bromomethyl-2-chloro-pyrimidine, the compounds 1-(5-Piperazin-1-yl-1H-indol-3-ylmethyl)-3,4-dihydro-1H-quinolin-2-one and 1-(2-Chloro-6-piperazin-1-yl-pyrimidin-4-ylmethyl)-3,4-dihydro-1H-quinolin-2-one were prepared.

Using the above procedure, but replacing piperazine in step 2 with the appropriate substituted piperazine, the following compounds were prepared:

1-(3-Methoxy-5-{4-[2-(4-methoxy-phenyl)-ethyl]-piperazin-1-yl}benzyl)-1H-quinolin-2-one;
  1-(3-{4-[2-(4-Fluorophenyl)-ethyl]-piperazin-1-yl}-5-methoxybenzyl)-1H-quinolin-2-one;
  1-{3-[4-(4,5-Dihydro-1H-imidazol-2-yl)-piperazin-1-yl]-5-methoxybenzyl}-1H-quinolin-2-one;
  1-[3-Methoxy-5-(4-pyrimidin-2-yl-piperazin-1-yl)-benzyl]-1Hquinolin-2-one;
  1-(3-{4-[2-(4-Fluoro-phenyl)-ethyl]-piperazin-1-yl}-5-methoxy-benzyl)-8-methoxy-1H-quinolin-2-one;
  1-(3-{4-[2-(4-Fluoro-phenoxy)-ethyl]-piperazin-1-yl}-5-methoxy-benzyl)-1H-quinolin-2-onee; and
  8-Methoxy-1-(3-methoxy-5-{4-[2-(4-methoxy-phenyl)-ethyl]-piperazin-1-yl}-benzyl)-1H-quinolin-2-one.

Example 2

4-(3-Chloro-5-piperazin-1-yl-benzyl)-7-methoxy-4H-benzo[1,4]oxazin-3-one

The synthetic procedures described in this Example were carried out according to the process shown in Scheme F. In this example, the 7-methoxy-1,4-benzoxazin-3-one used in Step 1 was prepared by the well known procedure described in Heterocycles (1983), Vol. 20(8), pp. 1481–1485.

SCHEME F

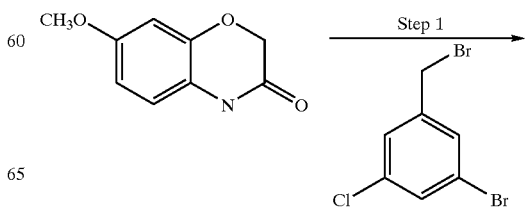

-continued

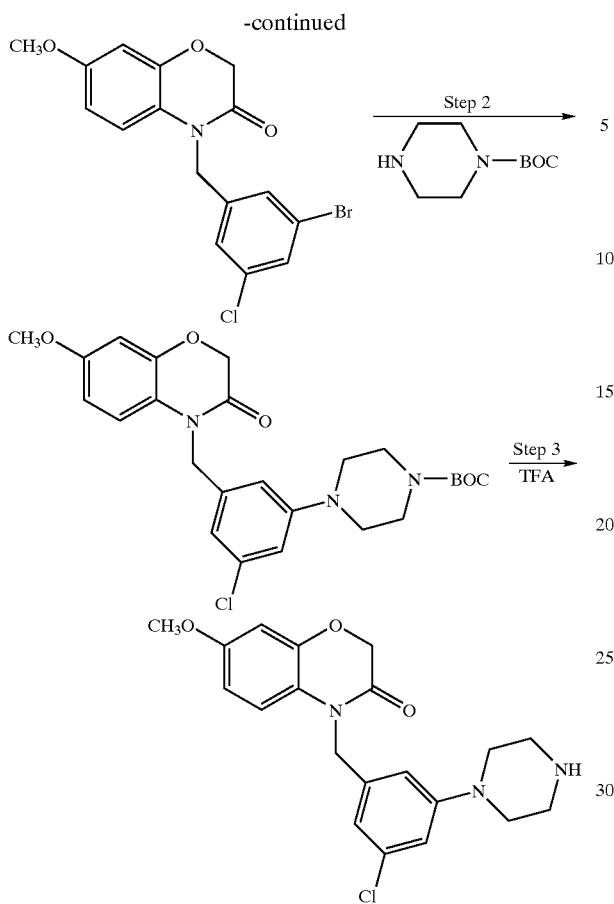

Step 1
4-(3-Bromo-5-methoxy-benzyl)-7-methoxy-4H-benzo[1,4]oxazin-3-one 0.5 grams of 7-methoxy-1,4-benzoxazin-3-one (2.8 mmole) was dissolved in 10 ml of dimethylformamide and cooled in an ice bath. 0.17 grams (3.5 mmole) of sodium hydride (60% wt. inn oil) was added, and after 5 minutes 0.8 grams (2.9 mmole) of 3-bromo-5-chloro-benzylbromide was added all at once. The mixture was stirred at ice bath temperature for 1 hour, and then quenched by addition of 1% hydrochloric acid. The product was extracted with ethyl acetate, that was evaporated under reduced pressure to give an oil which was chromatographed via medium pressure eluting with 10% ethyl acetate in hexanes to yield 0.9 grams of 4-(3-bromo-5-chloro-benzyl)-7-methoxy-4H-benzo[1,4]oxazin-3-one as a white solid.

Step 2
4-[3-Chloro-5-(4-Boc-piperazin-1-yl)-benzyl]-7-methoxy-4H-benzo[1,4]oxazin-3-one

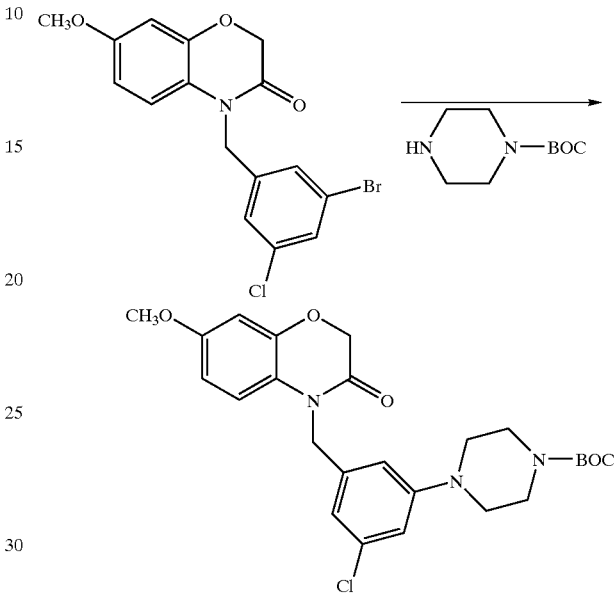

The reaction of 4-(3-bromo-5-methoxy-benzyl)-7-methoxy-4H-benzo[1,4]oxazin-3-one with 1-Boc-piperazine was carried out using the procedure described above in Example 1, Step 2.

Step 3
4-(3-Chloro-5-piperazin-1-yl-benzyl)-7-methoxy-4H-benzo[1,4]oxazin-3-one

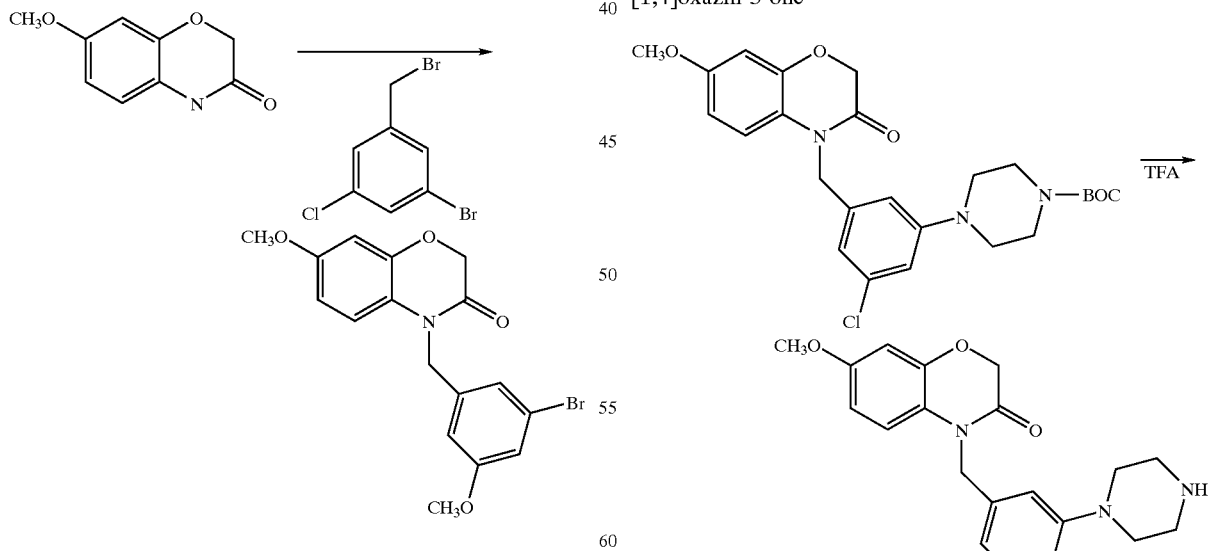

The deprotection of 4-[3-chloro-5-(4-Boc-piperazin-1-yl)-benzyl]-7-methoxy-4H-benzo[1,4]oxazin-3-one was carried out using the procedure described above in Example 1, Step 3, to yield 0.55 grams of 4-(3-Chloro-5-piperazin-1-yl-benzyl)-7-methoxy-4H-benzo[1,4]oxazin-3-one, M+H=389.

Example 3

1-(3-Piperazin-1-yl-benzyl)-1,3,4,5-tetrahydrobenzo[b]azepin-2-one

The synthetic procedures described in this Example were carried out according to the process shown in Scheme G.

SCHEME G

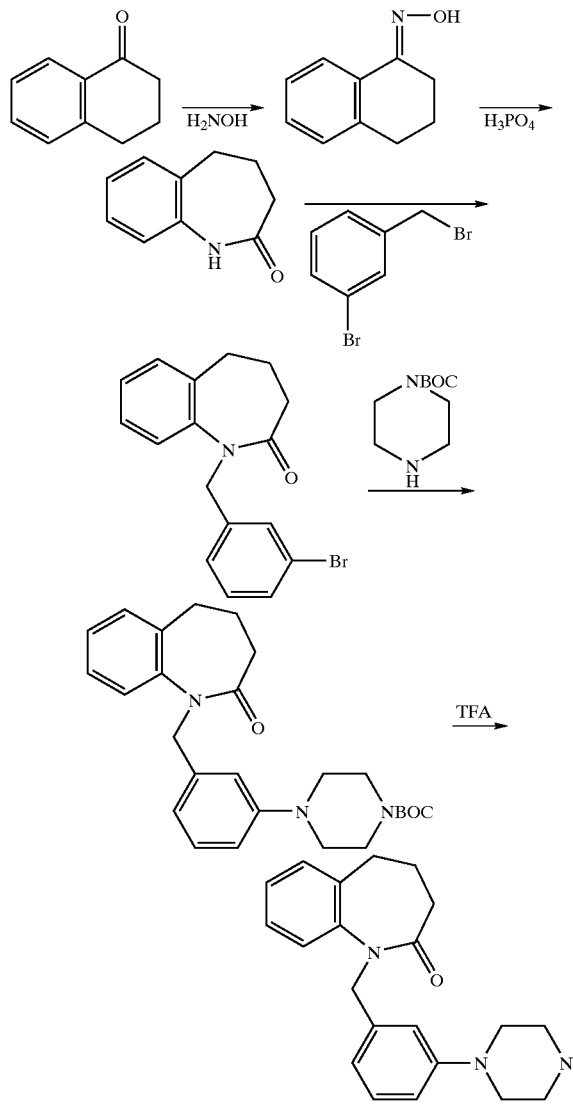

Step 1
1-Tetralone Oxime

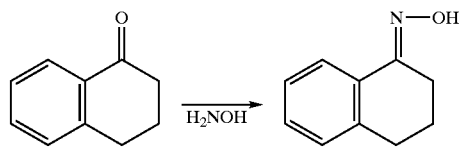

To a solution of 5 mL (37.5 mmole) 1-tetralone in 25 mL ethanol was added 2.7 mL (40 mmole) of 50% hydroxylamine in water. The reaction mixture was heated under reflux for 2 hrs, then stirred at room temperature for 16 hrs. The solution was concentrated under reduced pressure. The residue was recrystallized from toluene/hexane to give 1-tetralone oxime (3,4-dihydro-2H-naphthalen-1-one oxime), 3.86 g, m.p. 101–102°.

Step 2

1,3,4,5-Tetrahydro-benzo[b]azepin-2-one

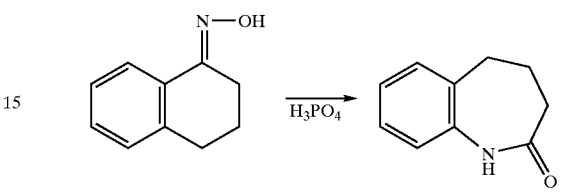

A mixture of 1.0 g (6.2 mmole) of 1-tetralone oxime and 10 g polyphosphoric acid was heated at 105° for 1 hr. The warm mixture was poured into 100 mL water with stirring. The pH was carefully adjusted to 6–7 by addition of solid sodium bicarbonate and the mixture was extracted with 60 mL ethyl ether. The organic phase was washed with 10 mL saturated sodium chloride, dried (MgSO$_4$) and concentrated under reduced pressure. The residue was recrystallized from ether/hexane to give 1,3,4,5-Tetrahydro-benzo[b]azepin-2-one, 0.682 g, m.p. 141–142°.

Step 3

1-(3-Bromo-benzyl)-1,3,4,5-tetrahydro-benzo[b]azepin-2-one

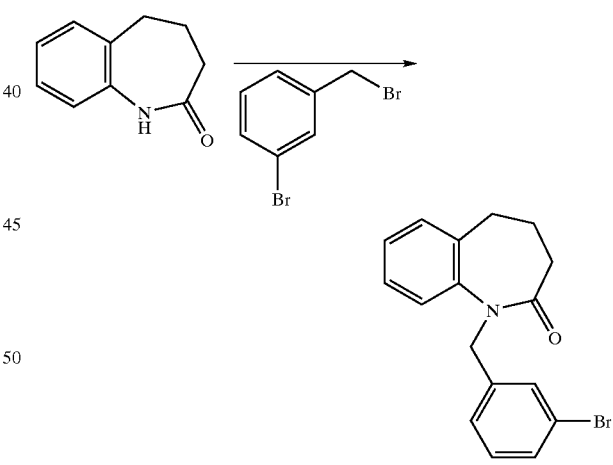

To a stirred mixture of 0.1 g (4 mmole) sodium hydride and 0.75 g (3.0 mmole) 3-bromobenzyl bromide in 5 mL dimethylformamide was added 0.438 g (2.72 mmole) solid 1,3,4,5-tetrahydro-benzo[b]azepin-2-one. The mixture was cooled in a water bath, then it was stirred at 23° for 1 hr. The solvent was removed under reduced pressure and the residue was partitioned between 30 mL ethyl acetate and 5 mL water. The organic phase was washed with 5 mL water, 5 mL saturated sodium chloride, dried (mgSO$_4$) and concentrated under reduced pressure. The residue was recrystallized from hexane to provide the title compound, 0.658 g, m.p. 81–82°.

Step 4
4-[3-(2-Oxo-2,3,4,5-tetrahydro-benzo[b]azepin-1-ylmethyl)-phenyl]-piperazine-1-carboxylic acid tert-butyl ester

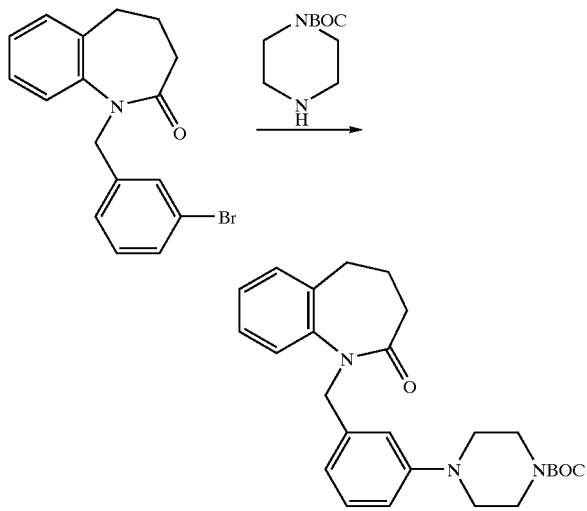

A mixture of 0.5 g (1.51 mmole) 1-(3-bromo-benzyl)-1,3,4,5-tetrahydro-benzo[b]azepin-2-one, 0.203 g sodium tert-butoxide, 0.04 g (0.16 mmole) tri-tert-butyl phosphine, 0.04 g (0.16 mmole) palladium(II)acetate, and 0.3 g piperazin-1-yl carboxylic acid tert-butyl ester in 5 mL xylene was heated at 105° under N$_2$ for 1.5 hrs. The mixture was diluted with 5 mL ethyl ether and then filtered through a pad of 10 g silica gel 230–400 mesh. 4-[3-(2-Oxo-2,3,4,5-tetrahydro-benzo[b]azepin-1-ylmethyl)-phenyl]-piperazine-1-carboxylic acid tert-butyl ester was eluted with 20% ethyl acetate/hexane to yield 0.64 g of a heavy syrup. M+H=436.

Step 5
1-(3-Piperazin-1-yl-benzyl)-1,3,4,5-tetrahydrobenzo[b]azepin-2-one

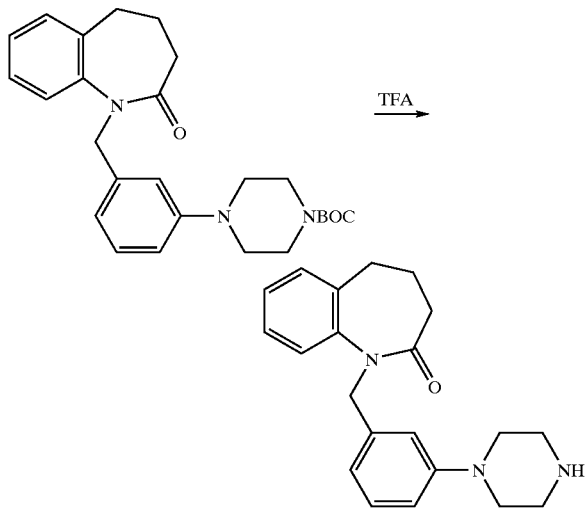

A solution of 0.6 g (1.38 mmole) 4-[3-(2-oxo-2,3,4,5-tetrahydro-benzo[b]azepin-1-ylmethyl)-phenyl]-piperazine-1-carboxylic acid tert-butyl ester in 3 mL trifluoroacetic acid was concentrated under reduced pressure. The residue was partitioned between 10 mL saturated sodium carbonate containing 1 mL 5% sodium hydroxide and 35 mL ethyl acetate. The organic phase was dried (MgSO$_4$) and concentrated under reduced pressure. The residue was converted to the maleate salt and recrystallized from methanol/ethyl acetate to provide 1-(3-Piperazin-1-yl-benzyl)-1,3,4,5-tetrahydrobenzo[b]azepin-2-one as a maleate salt, 0.346 g, m.p. 149–150°.

Example 4

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 5

Radioligand Binding Studies

This example illustrates in vitro radioligand binding studies of compound of formula I.

The binding activity of compounds of this invention in vitro was determined as follows. Duplicate determinations of ligand affinity are made by competing for binding of [$^3$H]LSD in cell membranes derived from HEK293 cells stably expressing recombinant human 5-HT6 receptor. This cell line was prepared by the method described by Monsma et al., *Molecular Pharmacology*, Vol. 43 pp. 320–327 (1993).

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [$^3$H] LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [$^3$H]LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{\text{Bmax} - \text{basal}}{1 + 10^{-Hill(\log[\text{ligand}] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT6 antagonists. The compound 1-(3-methoxy-5-piperazin-1-yl-benzyl)-3,4-dihydro-1H-quinolin-2-one, for example, exhibited a pKi for 5-HT6 of approximately 9.0 using the above procedure.

Example 6

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

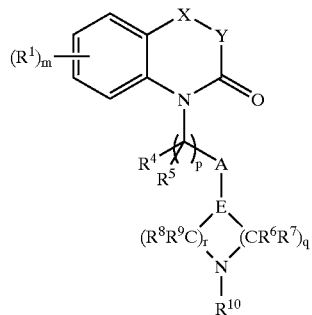

I and pharmaceutically acceptable salts or prodrugs thereof, wherein:
m is from 0 to 4;
p is from 1 to 3;
q is from 1 to 3;
r is from 1 to 3;
A is optionally substituted arylene;
E is N;
X is —$CR^aR^b$— wherein $R^a$ and $R^b$ each independently is hydrogen or alkyl;
each $R^1$ independently is halo, alkyl, haloalkyl, hydroxy, nitro, alkoxy, cyano, —$S(O)_sR^c$, —$NR^cR^d$, —$C(=O)$—$NR^cR^d$, —$SO_2$—$NR^cR^d$—$N(R^c$—$C(=O)$—$R^d$ or —$C(=O)$—$R^c$, wherein s is from 0 to 2 and $R^c$ and $R^d$ each independently is hydrogen or alkyl;
Y is —$(CR^2R^3)_n$— wherein n is 1 or 2 and $R^2$ and $R^3$ each independently is hydrogen or alkyl, or X and Y together form a —CH=CH— group;
$R^4$, $R^5$, $R^6$, $R^7$, $R^8$, and $R^9$ each independently is hydrogen or alkyl; and
$R^{10}$ is hydrogen, alkyl, arylalkyl, or aryloxyalkyl.

2. The compound of claim 1, wherein Y is —$(CR^2R^3)_n$— and n is 1.

3. The compound of claim 1, wherein Y is —$(CR^2R^3)_n$— and n is 2.

4. The compound of claim 2, wherein A is optionally substituted phenylene.

5. The compound of claim 4, wherein $R^2$, $R^3$, $R^a$ and $R^b$ are hydrogen.

6. The compound of claim 4, wherein q is 2 and r is 2.

7. The compound of claim 4, wherein m is 0.

8. The compound of claim 4, wherein m is 1 and $R^1$ is halo or alkoxy.

9. The compound of claim 4, wherein A is halophenylene, haloalkylphenylene, alkylphenylene, cyclopentyloxyphenylene alkoxyphenylene or alkylenedioxyphenylene.

10. The compound of claim 4, wherein $R^6$, $R^7$, $R^8$ and $R^9$ are hydrogen.

11. The compound of claim 3, wherein A is optionally substituted phenylene.

12. The compound of claim 11, wherein $R^2$, $R^3$, $R^a$ and $R^b$ are hydrogen.

13. The compound of claim 11, wherein q is 2 and r is 2.

14. The compound of claim 11, wherein m is 0.

15. The compound of claim 11, wherein m is 1 and $R^1$ is halo or alkoxy.

16. The compound of claim 11, wherein A is halophenylene, haloalkylphenylene, alkylphenylene, alkoxyphenylene, cyclopentyloxyphenylene or alkylenedioxyphenylene.

17. The compound of claim 11, wherein $R^6$, $R^7$, $R^8$ and $R^9$ are hydrogen.

18. The compound of claim 4, wherein $R^{10}$ is hydrogen or alkyl.

19. The compound of claim 4, wherein $R^{10}$ is arylalkyl, or aryloxyalkyl.

20. The compound of claim 19, wherein $R^{10}$ is 2-(4-fluorophenyl)-ethyl or 2-(4-methoxyphenyl)-ethyl.

21. The compound of claim 1, wherein said compound is of the formula:

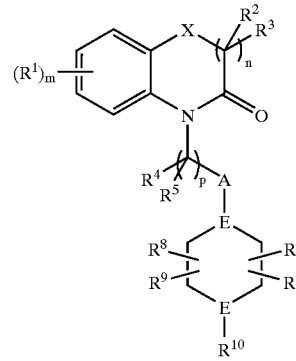

wherein m, n, p, X, A, E, $R^1$, $R^2$, $R^3$, $R^4$, $R^5$, $R^6$, $R^7$, $R^8$, $R^9$ and $R^{10}$ are as defined in claim 1.

22. The compound of claim 21, wherein said compound is of the formula:

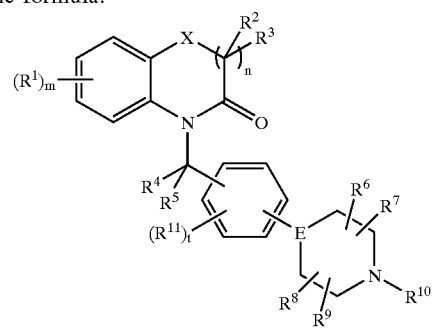

wherein t is from 0 to 4, each $R^{11}$ individually is halo, alkyl, haloalkyl, hydroxy, nitro, cyano or alkoxy, and m, n, X, E, $R^1$, $R^2$, $R^3$, $R^4$, $R^5$, $R^6$, $R^7$, $R^8$, $R^9$ and $R^{10}$ are as defined in claim 21.

23. The compound of claim 22, wherein said compound is of the formula:

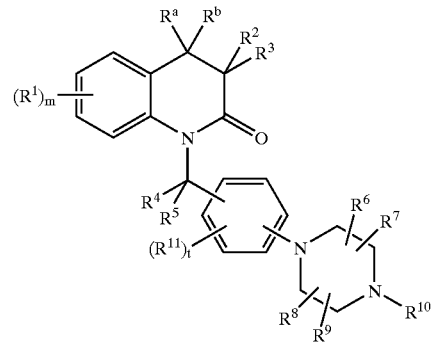

wherein m, t, $R^1$, $R^2$, $R^3$, $R^4$, $R^5$, $R^6$, $R^7$, $R^8$, $R^9$, $R^{10}$, $R^{11}$, $R^a$ and $R^b$ are as defined in claim 22.

24. The compound of claim 1, wherein said compound is of the formula:

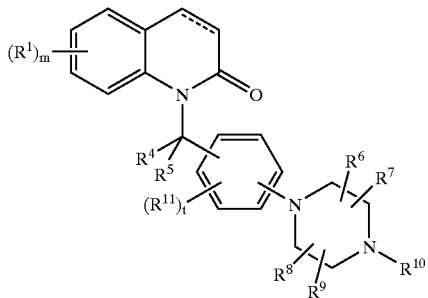

wherein — is an optional bond;
t is from 0 to 4;
each $R^{11}$ individually is halo, alkyl, haloalkyl, hydroxy, nitro, cyano or alkoxy; and
m, $R^1$, $R^4$, $R^5$, $R^6$, $R^7$, $R^8$, $R^9$, $R^{10}$ are as defined in claim 1.

25. The compound of claim 24, wherein said compound is of the formula:

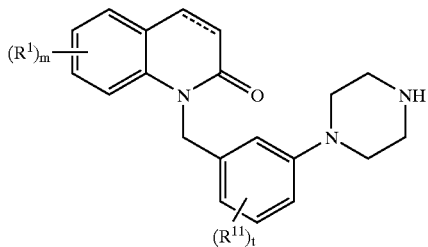

wherein — is an optional bond, and m, t, $R^1$ and $R^{11}$ are as defined in claim 24.

26. The compound of claim 25, wherein t is 0 or 1 and $R^{11}$ is halo, alkyl, haloalkyl or alkoxy.

27. The compound of claim 26, wherein $R^{11}$ is chloro, methyl, trifluoromethyl, methoxy or ethoxy.

28. The compound of claim 25, wherein t is 2 and the $R^{11}$ groups together define an alkylene dioxy radical.

29. The compound of claim 1, wherein said compound is selected from the group consisting of:

1-(3-Piperazin-1-yl-benzyl)-3,4-dihydro-1H-quinolin-2-one;
1-(4-Methoxy-3-piperazin-1-yl-benzyl)-3,4-dihydro-1H-quinolin-2-one;
1-(3-Chloro-5-piperazin-1-yl-benzyl)-3,4-dihydro-1H-quinolin-2-one;
1-(3-Methoxy-5-piperazin-1-yl-benzyl)-3,4-dihydro-1H-quinolin-2-one;
6-Chloro-1-(3-chloro-5-piperazin-1-yl-benzyl)-3,4-dihydro-1H-quinolin-2-one;
1-(3-Cyclopentyloxy-5-piperazin-1-yl-benzyl)-3,4-dihydro-1H-quinolin-2-one;
1-(3-Hydroxy-5-piperazin-1-yl-benzyl)-3,4-dihydro-1H-quinolin-2-one;
1-(3-Ethoxy-5-piperazin-1-yl-benzyl)-3,4-dihydro-1H-quinolin-2-one;
1-[3-Methoxy-5-(4-methylpiperazin-1-yl)-benzyl]-3,4-dihydro-1H-quinolin-2-one;
1-(7-Piperazin-1-yl-2,3-dihydro-benzo[1,4]dioxin-5-ylmethyl)-3,4-dihydro-1H-quinolin-2-one;
1-(3-Piperazin-1-yl-5-trifuoromethyl-benzyl)-3,4-dihydro-1H-quinolin-2-one;
1-(2-Chloro-5-piperazin-1-yl-benzyl)-3,4-dihydro-1H-quinolin-2-one;
1-(3-Methyl-5-piperazin-1-yl-benzyl)-3,4-dihydro-1H-quinolin-2-one;
8-Methoxy-1-(3-Methoxy-5-piperazin-1-yl-benzyl)-3,4-dihydro-1H-quinolin-2-one;
1-(2-Methoxy-3-piperazin-1-yl-benzyl)-3,4-dihydro-1H-quinolin-2-one;
1-(3-Piperazin-1-yl-benzyl)-1,3,4,5-tetrahydrobenzo[b]azepin-2-one;
1-(3-Methoxy-5-piperazin-1-yl-benzyl)-1H-quinolin-2-one;
1-(2-Methoxy-3-piperazin-1-yl-benzyl)-3,4-dihydro-1H-quinolin-2-one;
1-(3-Methoxy-5-{4-[2-(4-methoxy-phenyl)-ethyl]-piperazin-1-yl}benzyl)-1H-quinolin-2-one;
1-(3-{4-[2-(4-Fluorophenyl)-ethyl]-piperazin-1-yl}-5-methoxybenzyl)-1H-quinolin-2-one;
1-(3-{4-[2-(4-Fluoro-phenyl)-ethyl]-piperazin-1-yl}-5-methoxy-benzyl)-8-methoxy-1H-quinolin-2-one;
1-(3-{4-[2-(4-Fluoro-phenoxy)-ethyl]-piperazin-1-yl}-5-methoxy-benzyl)-1H-quinolin-2-one; and
8-Methoxy-1-(3-methoxy-5-{4-[2-(4-methoxy-phenyl)-ethyl]-piperazin-1-yl}-benzyl)-1H-quinolin-2-one.

30. A pharmaceutical composition comprising an efficacious amount of the compound of claim 1 in admixture with a pharmaceutically acceptable carrier.

31. A method for treating a HT6 antagonist-mediated disease state in a subject, said disease state selected from the group consisting of Parkinson's disease, Huntington's disease, manic depression, psychoses, Alzheimer's disease and memory disorders, said method comprising administering to said subject a therapeutically effective amount of a compound of claim 1.

32. A method for preparing a quinolinone compound, said method comprising:
reacting a compound of the formula x:

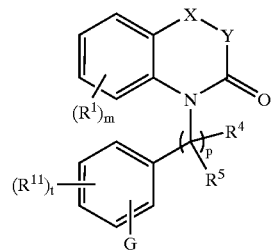

wherein:
X is —$CR^aR^b$—, wherein $R^a$ and $R^b$ each independently is hydrogen or alkyl;
m is from 1 to 4;
n is 1 or 2;
p is from 0 to 3;
t is from 1 to 4;
G is a leaving group;
each $R^1$ independently is halo, alkyl, haloalkyl, hydroxy, nitro, alkoxy, cyano, —$S(O)_sR^c$, —$NR^cR^d$, —$C(=O)$—$NR^cR^d$, —$SO_2$—$NR^cR^d$—$N(R^c$—$C$ (=O)—$R^d$ or —C(=O)—$R^c$ where s is from 0 to 2 and $R^c$ and $R^d$ each independently is independently hydrogen or alkyl;

Y is —$(CR^2R^3)_n$— wherein n is 1 or 2 and $R^2$ and $R^3$ each independently is hydrogen or alkyl, or X and Y together form a —CH=CH— group;

$R^4$ and $R^5$, each independently is hydrogen or alkyl; and each $R^{11}$ individually is halo, alkyl, haloalkyl, hydroxy, nitro, cyano or alkoxy;

with a heterocyclic amine of the formula f:

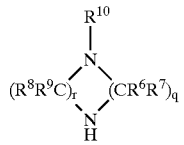

f wherein:
q is from 1 to 3;
r is from 1 to 3; and $R^6$, $R^7$, $R^8$, $R^9$ and $R^{10}$ each individually is hydrogen or alkyl;

to form a compound of the formula XIII:

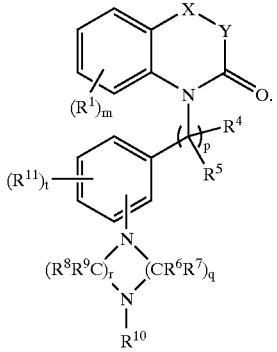

XIII

* * * * *